United States Patent [19]
Young

[11] Patent Number: 4,890,480
[45] Date of Patent: Jan. 2, 1990

[54] RELATING TO DEVICES FOR MEASURING FLUID DENSITY

[75] Inventor: Donald C. Young, Pangbourne, England

[73] Assignee: Thorn EMI plc, London, England

[21] Appl. No.: 237,808

[22] Filed: Aug. 29, 1988

[30] Foreign Application Priority Data

Aug. 28, 1987 [GB] United Kingdom ............. 8720355

[51] Int. Cl.[4] .............................................. G01N 9/00
[52] U.S. Cl. .................................................... 73/32 A
[58] Field of Search ........................... 73/30, 32 A, 579

[56] References Cited

U.S. PATENT DOCUMENTS

| | | | |
|---|---|---|---|
| 3,603,137 | 9/1971 | Banks | 73/30 |
| 3,648,512 | 3/1972 | Abbotts | 73/32 A |
| 3,842,655 | 10/1974 | Schlatter et al. | 73/32 A |
| 3,903,731 | 9/1975 | Sieben | 73/32 A |
| 3,903,732 | 9/1975 | Rork et al. | 73/32 A |
| 4,132,110 | 1/1979 | Muramoto | 73/32 A |
| 4,193,291 | 3/1980 | Lynnworth | 73/32 A |
| 4,297,872 | 11/1981 | Ikeda et al. | 73/32 A |
| 4,345,456 | 8/1982 | Ponzi | 73/32 A |
| 4,507,705 | 3/1985 | Hoshino et al. | 73/579 |
| 4,526,480 | 7/1985 | Ward | 73/32 A |
| 4,535,638 | 8/1985 | Eer Nisse et al. | 73/862.59 |
| 4,655,075 | 4/1987 | Albert et al. | 73/32 A |
| 4,783,987 | 11/1988 | Hager et al. | 73/32 A |

FOREIGN PATENT DOCUMENTS

| | | | |
|---|---|---|---|
| 239703 | 7/1987 | European Pat. Off. | 73/32 A |
| 2639985 | 12/1977 | Fed. Rep. of Germany | 73/32 A |

Primary Examiner—William A. Cuchlinski, Jr.
Assistant Examiner—Diego F. F. Gutierrez
Attorney, Agent, or Firm—Fleit, Jacobson, Cohn, Price, Holman & Stern

[57] ABSTRACT

A device for measuring fluid density, the device comprising a silicon substrate having a micro-engineered cantilevered beam fabricated on it for use as a density sensor. The beam is at the end of a tube and has a contact manufactured on its end and a contact manufactured on the substrate below the contact. Means for causing said structure to vibrate and for detecting a characteristic of the vibration are provided, the characteristic being dependent on the density of the fluid to be measured.

6 Claims, 3 Drawing Sheets

RELATING TO DEVICES FOR MEASURING FLUID DENSITY

This invention relates to a device for measuring fluid density, and in particular to a micro-engineered device manufactured on a semiconductor substrate.

According to the invention there is provided a device for measuring fluid density, the device including a structure which can be made to vibrate in a fluid, means for causing said structure to vibrate and means for detecting a characteristic of the vibration, the characteristic being dependent on the density of the fluid to be measured.

In a preferred embodiment, the structure may be a micro-engineered structure, including, for example, a micro-engineered cantilever beam or leaf structure fabricated on a substrate of silicon, though other semiconductors or other materials could be used. The cantilever or leaf could be replaced by a diaphragm.

The device may comprise a micro-engineered structure fabricated on a semiconductor substrate wherein the substrate has a hole extending through the substrate and wherein the micro-engineered structure is located at one end of the hole.

According to a further aspect of the invention there is provided a method of measuring fluid density, the method including causing a structure to vibrate in a fluid and measuring a characteristic of the vibration, the characteristic being dependent on the density of the fluid.

An important aspect of this invention is the provision of a method whereby the fluid density can be measured in said manner whilst ensuring the effects of changing fluid viscosity are negligible.

The structure may be driven into vibration by a variety of forces derived optically, thermally, electrostatically or electromagnetically.

In order that the invention may be clearly understood and readily carried into effect, it will be described by way of example with reference to the accompanying drawings, of which:

Figure 1:
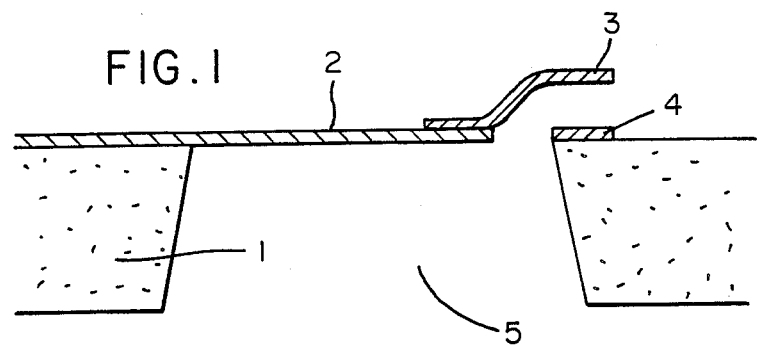
FIG. 1 shows a micro-engineered cantilever beam for use as a density sensor.

FIG. 1 shows a silicon substrate 1 having a micro-engineered cantilevered beam 2 fabricated on it for use as a density sensor. The beam is at the end of a tube 5 and has a contact 3 manufactured on its end and a contact 4 manufactured on the substrate below the contact 3.

Figure 2:
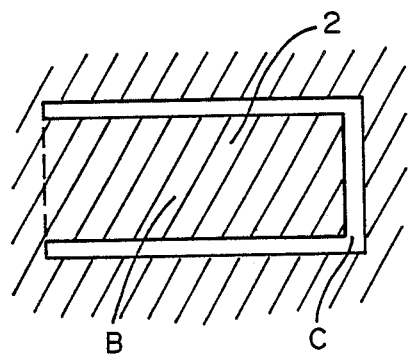
FIG. 2 shows a schematic plan view of a cantilever beam as in FIG. 1 (end contacts not shown)

FIG. 2 is a plan view of the cantilever 2 of FIG. 1 (end contacts not shown). The sensitivity of the device depends on the area B of the beam in relation to the surrounding area C. For greater sensitivity, the ratio of B:C should be large.

Figure 3:
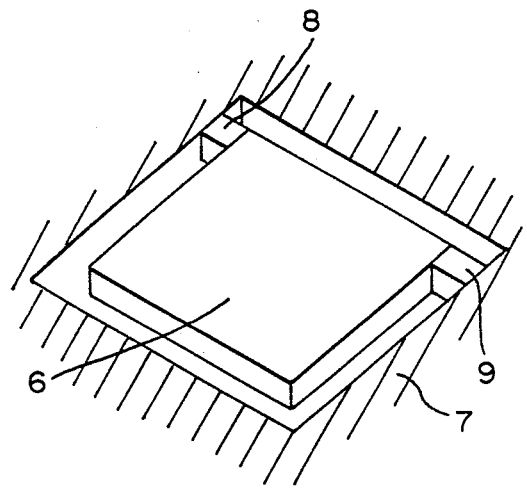
FIG. 3 represents a leaf for use as a density sensor.
Figure 4:
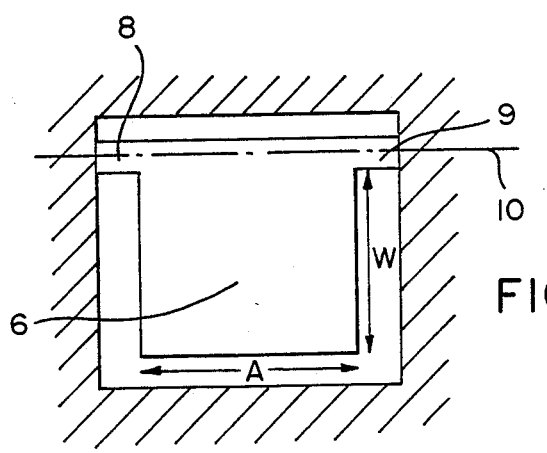
FIG. 4 shows a schematic plan view of the leaf of FIG. 3.

FIG. 3 represents a leaf 6 manufactured on a substrate 7 supported by side arms 8 and 9. The side arms are anchored at the ends joined to the substrate. FIG. 4 shows a plan view of the leaf which twists about an axis 10. It is of length W and width A.

The equation of motion for a cantilever or leaf vibrating in a stationary fluid is described by:

$$m\ddot{x} + R\dot{x} + Kx = F_D \tag{i}$$

where $m$ = effective mass at end of cantilever, or mass moment of inertia of a leaf (if the cantilever has a mass on its free end then $m \simeq$ mass on free end $+ \frac{1}{6}$ mass of cantilever, if leaf has a mass on its free and this should be added to mass moment of inertia).

$R$ = frictional damping constant of fluid in which the device vibrates, $K$ = "spring constant" of the vibrating structure, and $F_D$ = any force driving the device into operation.

$X$ = amplitude of vibration.

The response of such a device with frequency can be derived from (i) and equals:

$$x = \frac{F_D}{[K^2 + w^4 m^2 - 2w^2 Km + R^2 w^2]^{1/2}} \tag{ii}$$

$w = 2\pi f$ where f is the frequency of vibration.
amplitude of vibration (x) will be a maximum when:

$$w_R = \sqrt{\frac{K}{m} - \frac{R^2}{4m^2}} \tag{iv}$$

The value of K for the cantilever is given by:

$$K = \frac{Ybt^3}{4l^3} \tag{v}$$

where $Y$ = Young's modulus of elasticity, $b$ = width of cantilever, $t$ = thickness of cantilever, and $l$ = length of cantilever.

The value of K for the leaf is given by:

$$K = \frac{2Gdt^3}{3l} \tag{vi}$$

Where $G$ = shear modulus of elasticity, $t$ = thickness of side arms, $d$ = width of side arms, and (see FIG. 3)

$l$ = length of side arms.

The effective mass $m_L$ of the leaf for insertion into (ii) and (iv) is given by:

$$m_L = A^2 W^4 \rho_m t + 2\rho_m L^2 d^4 t \tag{vii}$$

where $\rho_m$ = density of leaf material, and d; t, A and W are shown in FIG. 4.

If the leaf has an end contact of mass $m_c$ at its free end then $m = m_L + m_c$.

Referring to (iii), if $w = w_R$, (i.e. the structure vibrated at its resonant frequency) then substitution in (iii) gives $$x = \frac{F_D}{w_R R} \quad \text{(viii)}$$

At low pressures, R can be derived from kinetic theory and is given by:

$$R_G = 8A\rho_G > \frac{kT}{2\pi m_S} \quad \text{(ix)}$$

where
$\rho_G$ = density of fluid in which the structure vibrates
k = Boltzmann's constant,
T = absolute temperature,
A = area of vibrating surface, and
$m_s$ = mass of gas molecules.

The value of R at higher pressures where the mean free path of gas molecules is small compared with the dimensions of the vibrating structure is not clear from the prior literature. However, a model can be derived which is believed to be applicable to many devices including those considered herein. The value of R from this is believed to be:

$$R_G = A\pi(2w\rho_G\mu)^{\frac{1}{2}} \quad \text{(x)}$$

where $\mu$ = coefficient of viscosity.

For a structure vibrating at its resonant frequency, the amplitude of vibration is given by expression (ii). However, it can be seen from expressions (ix) and (x) that the result obtained depends on the fluid constituents (which determine viscosity and mass), as well as on the fluid density $\rho_G$.

The device may be made sensitive to gas density but relatively insensitive to viscosity or molecular mass by judicious use of the sound waves emitted by the vibrating cantilever or leaf.

Figure 5:
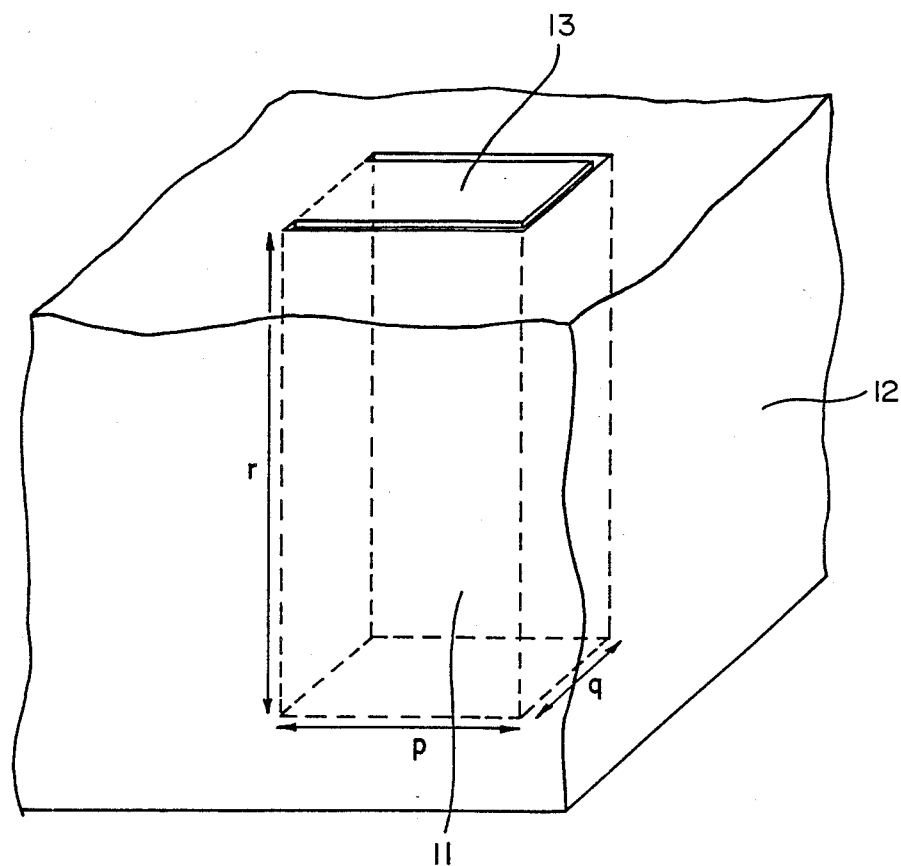
FIG. 5 is a schematic representation of a preferred embodiment of a device according to the invention.

FIG. 5 represents a preferred embodiment of a device, in which the vibrating structure (represented as a beam 13) is situated at the end of a tube 11 which is open at its opposite end. The dimensions of the tube are small compared with the wavelength of sound waves created in the fluid by the vibrating structure. In the illustrated embodiment the tube is a rectangular hole in the substrate 12 (which may be silicon) which can be fabricated using anisotropic etch techniques.

Typically, a rectangular tube may be 200 $\mu$m long, 100 $\mu$m wide and 400 $\mu$m deep (dimensions p, q and r respectively as shown in FIG. 5).

Sound waves generated by the vibrating cantilever or leaf will spread out rapidly in all directions at the open end of the hole. The gas near the end of the tube reacts on the wave and exerts a force on the vibrating structure proportional to the acceleration of the gas in the opening.

The force exerted back onto the vibrating structure is given by:

$$F = -i\left(\frac{S^2}{T}\right)\rho_G C \tan\left[\frac{2\pi r}{\lambda}\right]\frac{dy}{dt} \quad \text{(xi)}$$

where r is length of hole shown in FIG. 5, s = area of vibrating structure, T is cross sectional area of hole, $\lambda$ = wavelength of the sound waves.

A simple expansion of the tan factor and re-arrangement of terms shows that if $$\frac{2\pi r}{\lambda}$$

is less than 0.3 then (xi) becomes:

$$F = -i\left(\frac{S^2}{T}\right)\rho_G T \frac{d^2y}{dt^2} \quad \text{(xii)}$$

consideration of (i) will show that effective mass is now equal to:

$$m + \left(\frac{S^2}{T}\right)\rho_G T \quad \text{(xiii)}$$

This value of mass should be inserted in (i), (ii), (iv). Both resonant frequency and amplitude of vibration are proportional to gas density $\rho_G$.

The motion of the gas in the hole causes an additional friction force on the beam given by:

$$2(p+q)r(2\omega\mu\rho_G)^{1/2}\frac{dy}{dt} \quad \text{(xiv)}$$

The frictional constant should be added to R in (i), (ii), (iv) and (x).

Resonant frequency is now given by:

$$W_R = \quad \text{(xv)}$$

$$\sqrt{\frac{K}{M + \left(\frac{S^2}{T}\right)\rho_G T} - \frac{[2(p+q)r + MA]^2(2\mu\rho w)}{4\left[m + \rho_G r\left(\frac{S^2}{T}\right)\right]^2}}$$

By fabricating a cantilever or leaf of correct dimensions it has been found that the device may be made sensitive to gas density, but relatively insensitive to viscosity or molecular mass, by measurement of the change in resonant frequency (as described by xv).

Suitable devices can be fabricated by using microengineering techniques. A further advantage of a microengineered device is the fact that it can be fabricated using methods similar to standard integrated circuit techniques, which leads to low cost batch production. Further advantages are small size and the fact that sensing circuitry can be included on the same chip as the density sensor.

The gas density can also be measured by its effect on the amplitude of vibration (x). The frequency at which the amplitude is measured is chosen to give maximum discrimination between effects of density and effects of viscosity.

The invention is applicable to measurement of density of liquids as well as gases, but in the case of liquids the viscosity term may be more significant.

Figure 6:
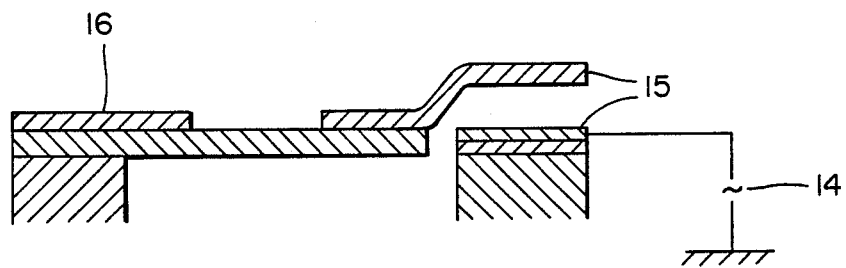
FIG. 6 is a schematic representation of a micro-engineered cantilever beam including means for causing the structure to vibrate and means for detecting a characteristic of vibration.

The driving force for causing the structure to vibrate may be an electrostatic force applied by providing a sine wave voltage 14 between contacts 15 fabricated at the end and below the end of the beam or leaf, such an arrangement is shown in FIG. 6. Any suitable drive circuit may be used. In this case the force $F_D$ is given by $$F_D = \frac{V_{IN} V_B \epsilon A}{y_B^2} \quad (xv)$$

where
- $V_{IN}$ = sine wave voltage height,
- $V_B$ = d.c. bias applied between end contacts,
- $\gamma$ = permittivity,
- A = area of overlap of end contacts, and
- $y_B$ = gap distance between end contacts.

It would also be possible to apply a square wave or pulses.

Another way of making a beam or leaf vibrate would be to apply a pulsed current to a resistive film placed on top of the beam, and the pulsed heating caused by the current would cause the beam to vibrate. A further method of making a beam or leaf vibrate is to apply optical pulses from a laser.

The fabrication of a micro-beam and end contacts is described in European Patent Application No. 86309946.1.

End contacts for a leaf can be made in the same way as described in that application, and the techniques for leaf fabrication are similar to those for beam fabrication. The leaf can be made from doped silicon or an insulator. The side arms 8 and 9 can be made from the same material as, or a different material from, the main mass. Silicon oxynitride (a material not usually used in integrated circuit fabrication) is a particularly suitable material for some purposes.

A suitable composition of silicon oxynitride to produce cantilevers leaves or side arms showing negligible stress, has a refractive index from 1.5 to 1.6, and preferably 1.53, and formed by the reaction between ammonia, silane, and nitric oxide and using atmospheric CVD techniques.

Another method of producing silicon oxynitride uses ammonia, silane and nitrous oxide in a low pressure CVD reactor, in which case the preferred refractive index is 1.8 to 1.9.

A leaf structure may be fabricated on a single crystal p-type silicon substrate. The main mass of the leaf may be silicon with silicon oxynitride on top. The silicon leaf can be delineated within an oxide mask and doped with boron to more than $10^{20}$ boron atoms/cm$^3$ by either diffusion or ion implantation. The diffused or implanted depth should be that required to obtain the desired thickness of leaf. The surface of the substrate is coated with the material and to the required thickness for the side arms.

The shape of the leaf and side arms is delineated within a photo-resist pattern and etched out using an anisotropic etch.

The "tube" is etched by masking and anisotropically etching from the back of the slice. The highly doped silicon and the side arm material are unaffected by the anistropic etch.

The amplitude of vibration can be measured directly by incorporating a material 16 responsive to stress on the microbeam or side areas of the flap. Such a material could be, for example, piezoelectric zinc oxide, or piezoresistive silicon (either polycrystalline or single crystal) and doped to obtain the desired characteristics. The amplitude of vibration can also be measured by the variation in a capacitance between the end contacts on the beam and below it.

I claim:

1. A device for measuring the density of a fluid, the device comprising:
   a semiconductor substrate;
   a micro-engineered structure which is manufactured on the semiconductor substrate and is adapted to be capable of vibration in the fluid;
   a hole having two ends extending through the substrate with the micro-engineered structure located at one end thereof, the dimensions of the hole being small compared with the wavelength of sound waves created in the fluid by the vibrating structure;
   means for causing the structure to vibrate and means for detecting a characteristic of said vibration, the said characteristic being dependent on the density of said fluid.

2. A device according to claim 1 in which the structure is a cantilever beam.

3. A device according to claim 1 in which the structure is a leaf.

4. A device according to claim 1 in which the semiconductor substrate is silicon.

5. A device according to claim 1, 2, 3 or 4 in which the hole has a rectangular cross section and the depth of the hole is perpendicular to the surface of the substrate.

6. A method of measuring fluid density, the method including causing a structure as described hereinbefore by claim 5 to vibrate in a fluid and measuring a characteristic of the vibration, the characteristic being dependent on the density of the fluid.

* * * * *